United States Patent
Dohrmann et al.

(10) Patent No.: US 12,261,871 B2
(45) Date of Patent: *Mar. 25, 2025

(54) REAL-TIME PRECISION CARE PLAN SUPPORT DURING REMOTE CARE MANAGEMENT

(71) Applicant: Electronic Caregiver, Inc., Las Cruces, NM (US)

(72) Inventors: Anthony Dohrmann, El Paso, TX (US); Bryan John Chasko, Las Cruces, NM (US); Juseung Park, Las Cruces, NM (US); Isaac Davalos, Las Cruces, NM (US)

(73) Assignee: Electronic Caregiver, Inc., Las Cruces, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/765,121

(22) Filed: Jul. 5, 2024

(65) Prior Publication Data

US 2024/0364726 A1 Oct. 31, 2024

Related U.S. Application Data

(63) Continuation of application No. 17/187,568, filed on Feb. 26, 2021, now Pat. No. 12,034,748.

(60) Provisional application No. 62/983,455, filed on Feb. 28, 2020.

(51) Int. Cl.
*H04L 9/40* (2022.01)
*G06N 5/043* (2023.01)
*G16H 40/67* (2018.01)
*G06N 20/10* (2019.01)

(52) U.S. Cl.
CPC ......... *H04L 63/1425* (2013.01); *G06N 5/043* (2013.01); *G16H 40/67* (2018.01); *G06N 20/10* (2019.01)

(58) Field of Classification Search
CPC .... H04L 63/1425; G16H 40/67; G06N 5/043; G06N 20/10
See application file for complete search history.

(56) References Cited

U.S. PATENT DOCUMENTS

| | | | |
|---|---|---|---|
| 10,983,841 B2 | 4/2021 | Walters et al. | |
| 11,257,587 B1 * | 2/2022 | D'Angelo | A61B 5/0022 |
| 11,322,250 B1 * | 5/2022 | Laster | A61B 5/681 |
| 11,323,196 B1 * | 5/2022 | Newton | H04J 3/1682 |
| 11,482,322 B1 * | 10/2022 | Bhansali | G16H 50/30 |

(Continued)

*Primary Examiner* — Stephen T Gundry
(74) *Attorney, Agent, or Firm* — Carr & Ferrell LLP

(57) ABSTRACT

Provided herein are exemplary embodiments including a secure intelligent networked architecture for real-time precision care plan remote support including a secure intelligent data receiving agent having a specialized hardware processor and a memory, the secure intelligent data receiving agent configured to automatically receive a digital data element over a network from a Bluetooth® equipped peripheral device, the digital data element representing an output in response to a predetermined plan, the secure intelligent data receiving agent caching the digital data element within a non-relational database for short term storage and the secure intelligent data receiving agent configured to process the digital data element using a serverless compute functionality and configured with logic for anomaly detection.

20 Claims, 6 Drawing Sheets

(56) References Cited

U.S. PATENT DOCUMENTS

| | | |
|---|---|---|
| 11,501,859 B1 * | 11/2022 | Guillén et al. ......... G16H 40/40 |
| 11,546,324 B1 | 1/2023 | Brooker et al. |
| 11,552,940 B1 | 1/2023 | Shahidzadeh et al. |
| 2004/0122704 A1 | 6/2004 | Sabol et al. |
| 2017/0193165 A1 | 7/2017 | Mandalika et al. |
| 2020/0085300 A1 | 3/2020 | Kwatra et al. |
| 2020/0143920 A1 | 5/2020 | Crosby |
| 2020/0364525 A1 | 11/2020 | Mats et al. |
| 2021/0257065 A1 * | 8/2021 | Mander .................. G16H 10/60 |
| 2021/0257093 A1 * | 8/2021 | Griffin ................... G16H 50/20 |
| 2021/0273962 A1 | 9/2021 | Dohrmann et al. |
| 2021/0287769 A1 * | 9/2021 | Dunleavy .............. G16H 10/60 |
| 2021/0319898 A1 * | 10/2021 | Kapoor .................. G16H 30/20 |
| 2021/0326128 A1 * | 10/2021 | Malladi .................. H04L 67/12 |
| 2021/0398627 A1 * | 12/2021 | Veliah .................... G16H 50/70 |
| 2022/0027504 A1 * | 1/2022 | Vom ...................... G06F 21/606 |
| 2022/0051276 A1 * | 2/2022 | Zelocchi ................. G16H 30/40 |
| 2022/0101968 A1 * | 3/2022 | Lancelot ............. G06F 21/6245 |
| 2022/0130525 A1 * | 4/2022 | Knoplioch ............. G16H 30/20 |
| 2022/0131699 A1 * | 4/2022 | Kimmel ............. H04L 63/0861 |
| 2022/0139550 A1 * | 5/2022 | Zhao ...................... G16H 10/60 705/3 |
| 2022/0165434 A1 * | 5/2022 | Do ......................... G16H 20/30 |
| 2022/0319696 A1 * | 10/2022 | Dohrmann ............. G16H 80/00 |
| 2022/0319713 A1 * | 10/2022 | Dohrmann ............. G16H 80/00 |
| 2022/0319714 A1 * | 10/2022 | Dohrmann ............. G16H 15/00 |
| 2022/0335339 A1 * | 10/2022 | Vegas Santiago ..... G06N 20/00 |
| 2022/0367054 A1 | 11/2022 | Gnanasambandam et al. |
| 2022/0377093 A1 | 11/2022 | Crabtree et al. |
| 2022/0384001 A1 | 12/2022 | Gnanasambandam et al. |
| 2022/0384003 A1 | 12/2022 | Gnanasambandam et al. |
| 2022/0384052 A1 | 12/2022 | Gnanasambandam et al. |
| 2022/0391270 A1 | 12/2022 | Gnanasambandam et al. |
| 2023/0019862 A1 | 1/2023 | Vines |
| 2023/0047253 A1 | 2/2023 | Gnanasambandam et al. |
| 2023/0052573 A1 | 2/2023 | Gnanasambandam et al. |
| 2023/0082381 A1 | 3/2023 | Gnanasambandam et al. |
| 2023/0116079 A1 | 4/2023 | Zhao et al. |
| 2023/0138557 A1 | 5/2023 | Laborde |
| 2023/0170069 A1 | 6/2023 | Groteke et al. |
| 2023/0215530 A1 | 7/2023 | McNair |

* cited by examiner

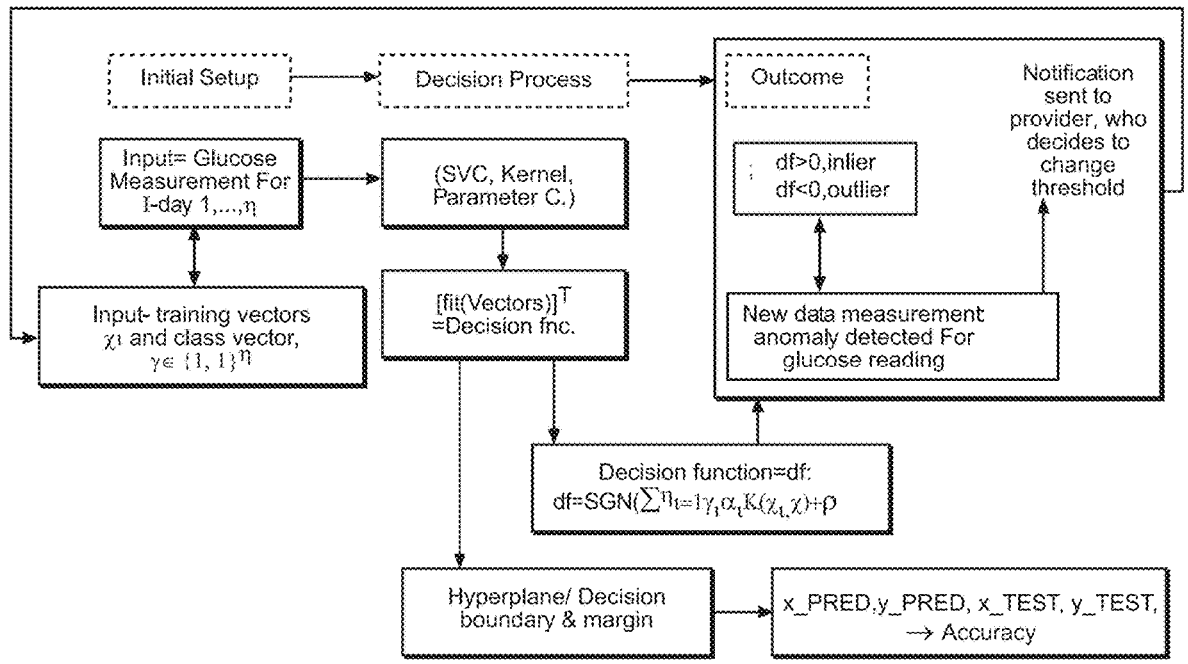
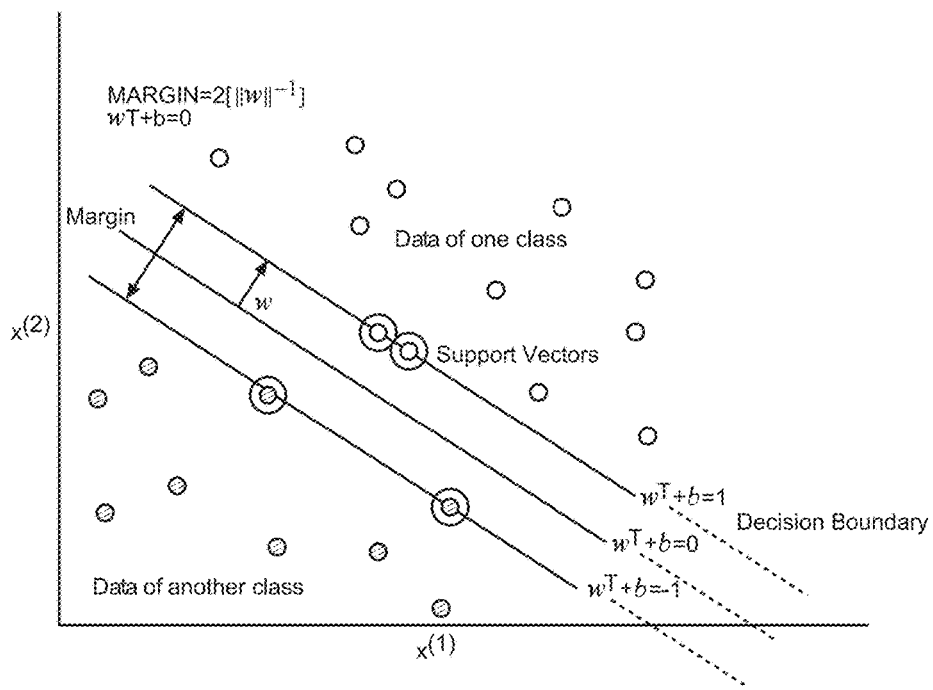
FIG. 2

| | | | | | |
|---|---|---|---|---|---|
| ⊙ addison core < | Seattle, WA | | | 🔒 Ⓐ Cypress | |
| 🏢 Office | Office/Active Alerts | | | | Export |
| Active Alert | Last updated 2/24/2021 3:28PM ↻ | | | | |
| Alert History | Timestamp | Patient | Type | Addressed | |
| 👤 Patient > | Feb 24, 2021 2:55:41PM | Libbie Funk | BPM | | Details |
| | Feb 24, 2021 2:30:43PM | Fern Koelpin | BPM | | Details |
| | Feb 24, 2021 2:28:42PM | Sibyl Smitham | Thermometer | | Details |
| | Feb 24, 2021 2:23:36PM | Magnolia Becker | BPM | | Details |
| | Feb 24, 2021 1:46:57AM | Alayna Klocko | BPM | | Details |
| | Feb 24, 2021 1:11:47PM | Alayna Klocko | BPM | | Details |
| | Feb 24, 2021 12:42:15PM | Fae Corwin | BPM | | Details |
| | Feb 24, 2021 11:30:37AM | Alayna Klocko | Thermometer | | Details |
| | Feb 24, 2021 10:51:19AM | Burley Champlin | BPM | | Details |
| | Feb 24, 2021 10:49:02AM | Dean Eichmann | WEIGHT | | Details |
| | Feb 24, 2021 10:12:06AM | Winfeild Hermann | BPM | | Details |
| ˅ | | | | Clear | Address |

FIG. 3

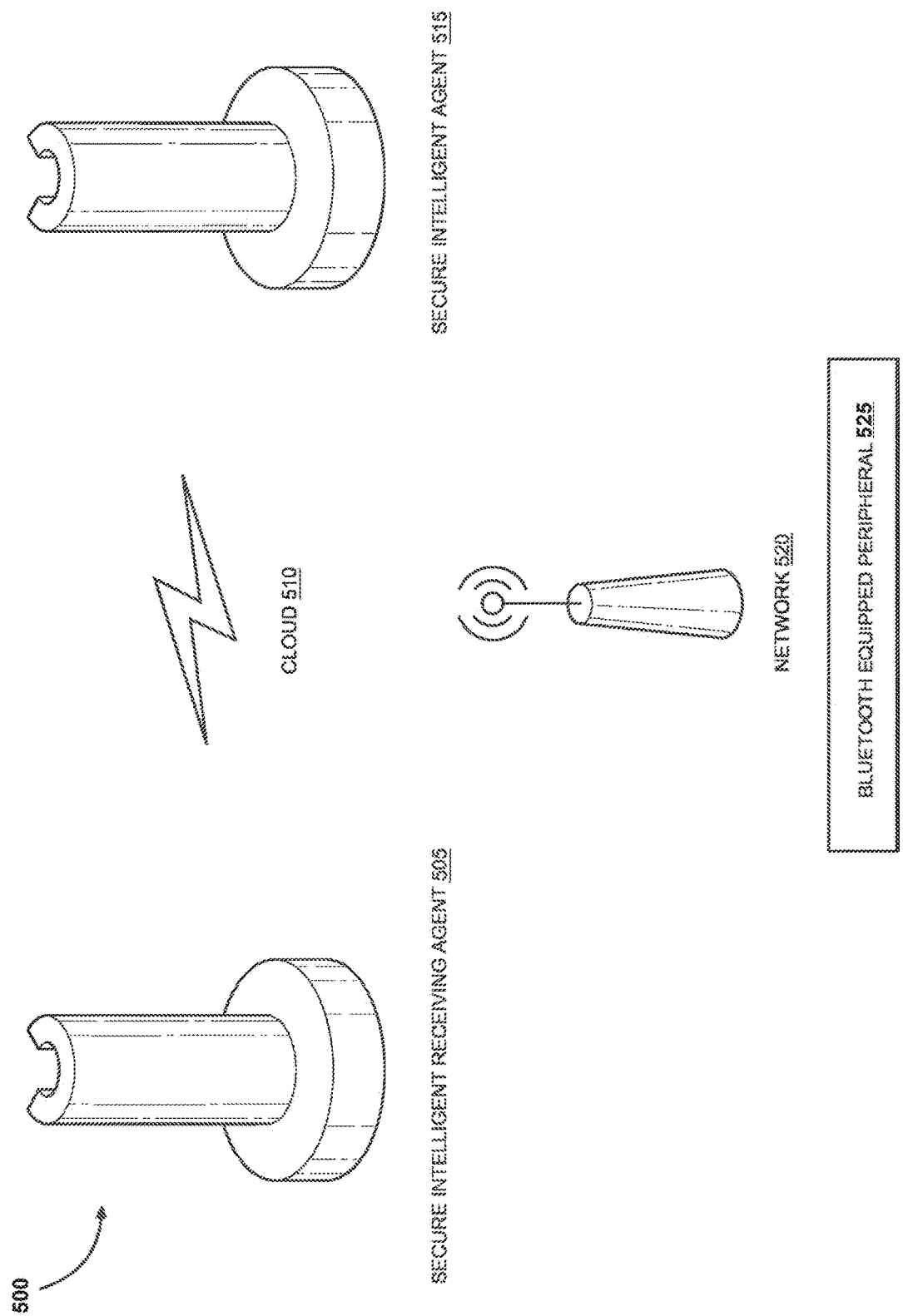

REAL-TIME PRECISION CARE PLAN SUPPORT DURING REMOTE CARE MANAGEMENT

CROSS-REFERENCE TO RELATED APPLICATIONS

This continuation application claims the priority benefit of U.S. Non-Provisional patent application Ser. No. 17/187,568 filed on Feb. 26, 2021 and titled, "An Intelligent Platform for Real-Time Precision Care Plan Support During Remote Care Management," which claims the priority benefit of U.S. Provisional Patent Application Ser. No. 62/983,455 filed on Feb. 28, 2020 and titled, "Intelligent Platform for Real-Time Precision Care Plan Support During Remote Care Management," all of which are hereby incorporated by reference in their entireties.

FIELD OF EXEMPLARY EMBODIMENTS

Exemplary embodiments relate to a technological platform for collecting, analyzing, interpreting, and transmitting remotely collected health data, focusing on the identification of data deemed anomalous and transmitting it over wireless communication networks.

SUMMARY OF EXEMPLARY EMBODIMENTS

Provided herein are exemplary embodiments including a secure intelligent networked architecture for real-time precision care plan remote support including a secure intelligent data receiving agent having a specialized hardware processor and a memory, the secure intelligent data receiving agent configured to automatically receive a digital data element over a network from a Bluetooth® equipped peripheral device, the digital data element representing an output in response to a predetermined plan, the secure intelligent data receiving agent caching the digital data element within a non-relational database for short term storage and the secure intelligent data receiving agent configured to process the digital data element using a serverless compute functionality and configured with logic for anomaly detection.

The secure intelligent networked architecture for real-time precision plan remote support further comprises a secure intelligent data storage agent having a specialized hardware processor and a memory, the secure intelligent data storage agent configured to automatically store the digital data element if it is associated with a non-anomalous and/or anomalous detection. The secure intelligent networked architecture for real-time precision plan remote support includes the logic for anomaly detection configured to place the digital data element into a range if it is associated with a non-anomalous and/or anomalous detection. The logic for anomaly detection is also configured to adjust the range for a plurality of patients and configured to adjust the range for a single patient.

In further exemplary embodiments, the secure intelligent data receiving agent is configured with electronic healthcare records for a plurality of patients and configured to perform a risk stratification for a patient's capacity for self-managed care. In some exemplary embodiments, the risk stratification includes high risk, moderate risk, mild risk and low risk as the patient's capacity for successful self-management of the patient's current disease state.

Also provided is an interactive touchscreen graphical user interface-based content delivery system configured for interpretation of the digital data element if it is associated with an anomalous and/or non-anomalous determination. The logic for anomaly detection is also configured to simultaneously route the digital data element through the logic for anomaly detection a second time, through a cloud-based service for long-term storage and analysis, and to automatically notify a content delivery network if it is associated with an anomalous determination. Exemplary embodiments include the integration of a remotely collected digital data element and an electronic healthcare record within the secure intelligent data receiving agent by way of an encrypted application programming interface ("API").

In various exemplary embodiments, the output may include temperature, oxygen saturation, weight, blood glucose level, or blood pressure data. The Bluetooth® equipped peripheral device may be a glucose monitor, thermometer, pulse oximeter, blood pressure monitor, spirometer or a scale, and may be equipped with a hardware processor. Furthermore, the predetermined plan may be stored on a networked computing device and the secure intelligent data receiving agent may be configured to change the predetermined plan based on the output. The secure intelligent data receiving agent may be configured to change the predetermined plan based on the anomaly or non-anomaly and the secure intelligent data receiving agent may be configured to change the predetermined plan based on the stratification. Additionally, the secure intelligent data receiving agent is configured to change the predetermined plan based on a range.

BRIEF DESCRIPTION OF THE DRAWINGS

FIG. 2 is a depiction of anomaly detection according to exemplary systems and methods of the present technology.

FIG. 3 is a depiction of active alerts resulting from anomaly detection according to exemplary systems and methods of the present technology.

FIG. 5 is a depiction of an exemplary secure intelligent networked architecture according to exemplary systems and methods of the present technology.

DESCRIPTION OF EXEMPLARY EMBODIMENTS

It should be understood that the disclosed embodiments are merely exemplary, which may be embodied in multiple forms. Those details disclosed herein are not to be interpreted in any form as limiting, but as the basis for the claims.

Tracking patient health outside of healthcare clinics has historically relied on reporting data long after it has been captured, usually by having patients physically write down the results of their health testing, and then bringing the data into their next appointment so that the results could be analyzed. Some newer technology allows patients the ability to record their results, and then manually email it to their healthcare provider for review. However, both methods require patients to report the data to their physicians, and the physicians then need to sift through all of the data to identify any anomalies for each individual patient, as well as factoring in what would be considered anomalous for each patient. Therefore, the exemplary embodiments disclosed herein have been developed to streamline this process and enable healthcare providers to have immediate notification of any anomalous data. They are designed to record all data and call immediate attention to that data which are considered outside of normal range so that healthcare providers can prioritize their interactions as needed for those with dangerous anomalies.

It is an object of the exemplary embodiments herein to provide individuals with near real-time, remotely collected health data from which current care plan assessment and alteration can be completed in support of an individual's healthcare needs. Also provided are real-time notifications when ingested data are observed to be outside of a defined range, as well as risk stratification for population groups based on detected anomalies. As such, it functions to provide real-time insight and notifications related to an individual's adherence to and progression through their prescribed plan of care. Additionally, the integrated real-time anomaly detection coupled with the notification and feedback functionality provides the capacity for remote inclusion of care providers in the day-to-day assessment and decision-making related to care plan adherence and progress outside of the care facility. All ingested health data are also routed to a cloud-based system capable of providing a graphical user interface for display of historical patient data for in-depth analysis and with the capability of further integration into existing electronic medical records systems. With the capabilities identified herein, the ecosystem of patient care is improved by providing actionable data to users.

Figure 1:
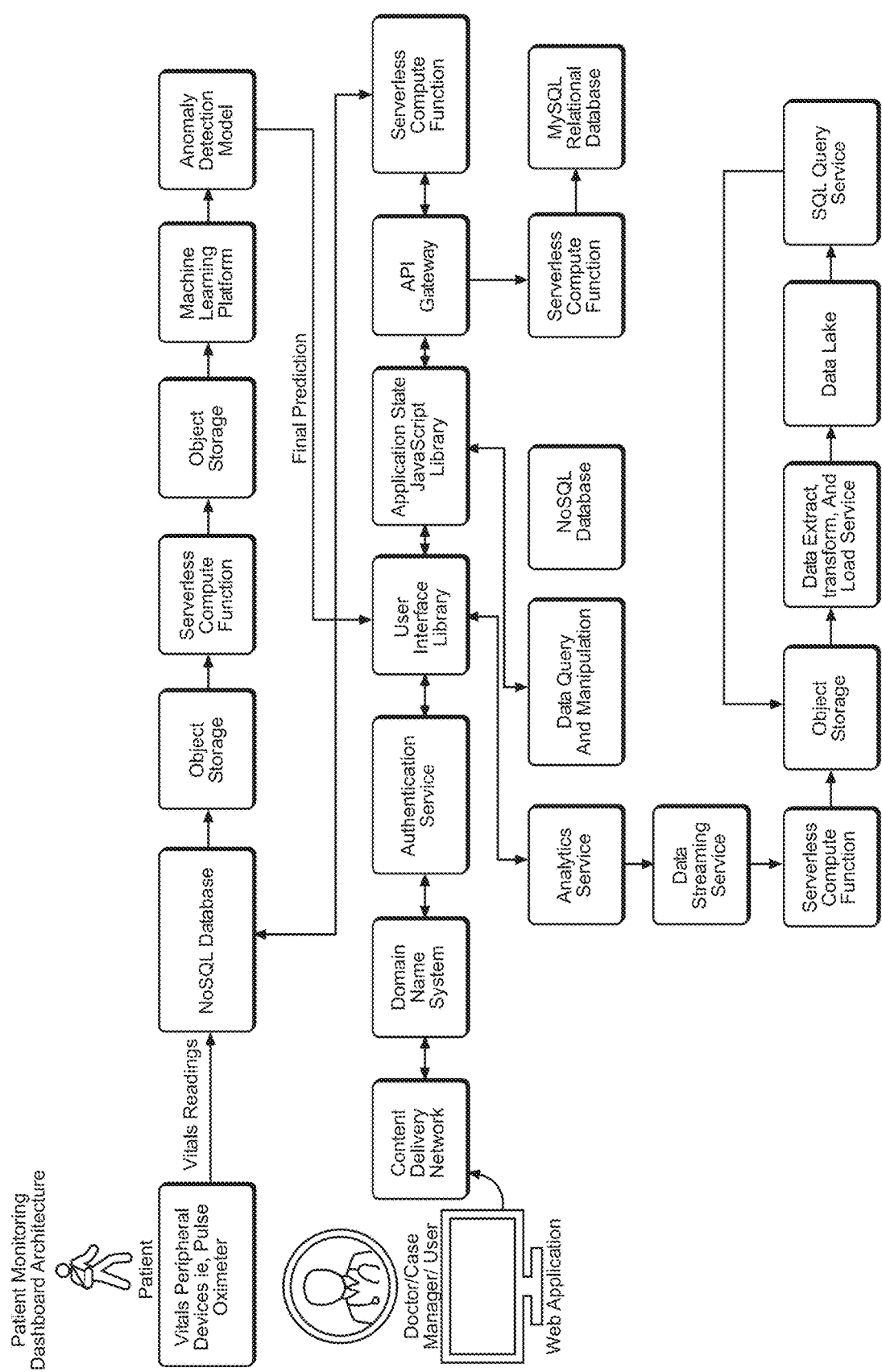
FIG. 1 is a platform overview according to exemplary systems and methods of the present technology.

FIG. 1 is a platform overview according to exemplary systems and methods of the present technology.

Referring to FIG. 1, in a setting detached from a standard care provision facility, the user collects relevant healthcare related data as prescribed by one or more of their current healthcare providers. These health data are collected via one or more Bluetooth® equipped peripheral devices. The collected health data are transmitted to a centrally positioned smart hub that connects to either the Internet or a cellular network. Once ingested into the smart hub, health data are securely transmitted via the Internet or a cellular network to a series of cloud-based services. Throughout the processes, all data are secured using AES-256-bit encryption, whether data are in transit or at rest.

Those health data from the user that are ingested are processed locally upon ingestion and routed via two pathways for retention and additional analyses. Firstly, ingested health data from the user are cached within a non-relational database for short term storage. Following this, data are processed using serverless compute functionality and routed for near real-time analysis using anomaly detection via machine learning. Following anomaly assessment, health data from the user are transmitted along one of two pathways. These pathways include: 1) long term data storage for non-anomalous findings, and 2) a proprietary graphical user interface-based content delivery system for provider access and interpretation for anomalous readings.

Anomaly Detection

FIG. 2 is a depiction of anomaly detection according to exemplary systems and methods of the present technology. The top of the figure is the process of using a machine learning ("ML") model that inputs such data as a user's vital signs and outputs a decision. This prompts the notification system. The bottom of the figure depicts the support vector machine classifier (SVC) that can detect anomalies by classifying outliers.

Immediately upon ingestion, health data from the user are prepared for anomalous magnitude evaluation using anomaly detection as depicted in FIG. 2. Non-anomalous ranges are defined by healthcare providers across the care plan. The platform is designed such that healthcare providers can define these non-anomalous ranges on a patient-by-patient basis, allowing for the algorithm to be refined across individuals as opposed to groups of patients. Once the non-anomalous range is defined, it may also be modified by healthcare providers as the user progresses through their plan of care, providing the platform with the capacity for being dynamic.

As health data are ingested, they are routed from non-relational storage to serverless compute functions which process them for anomaly detection analysis. Once processing has been completed, data are ingested into the cloud-based machine learning platform and routed to the appropriate anomaly detection algorithm. Data preprocessing and routing occur as a function of the algorithmic data architecture requirements and data tags. For those readings determined to fall within the provider defined non-anomalous range, data are routed to long-term storage. For those readings determined to fall outside of the provider defined non-anomalous range, data are still routed to long-term storage, and they are also immediately routed through a content delivery system and displayed via graphical user interface for remote review by the healthcare provider and/or staff of the healthcare provider.

Response to Anomalies

FIG. 3 is a depiction of active alerts resulting from anomaly detection according to exemplary systems and methods of the present technology.

The response process for when the platform uncovers an anomalous reading from the user is depicted in FIG. 3. When ingested data are deemed anomalous by the platform, the following three actions occur simultaneously: 1) the anomalous data are automatically routed back through the analysis for confirmation; 2) the anomalous data are automatically routed through the cloud-based services for long-term storage and analysis; and 3) a notification of observed anomaly is routed to the content delivery network and to healthcare providers, the user and additional 3rd parties identified by the user.

The design of this response process also allows for healthcare providers to receive notification of anomalous readings across multiple patients within their ecosystem as a provider. By integrating a user interface library system immediately following anomaly detection, the platform has the capacity for collating users and their data. In doing so, the platform automates the data analysis, presentation and notification of anomalies for multiple patients under a single provider. As such, healthcare providers have the capability to select receipt of notification of anomalous readings on a patient-by-patient basis, across designated classes of patients, or across all monitored patients simultaneously.

Graphical User Interface

Figure 4:
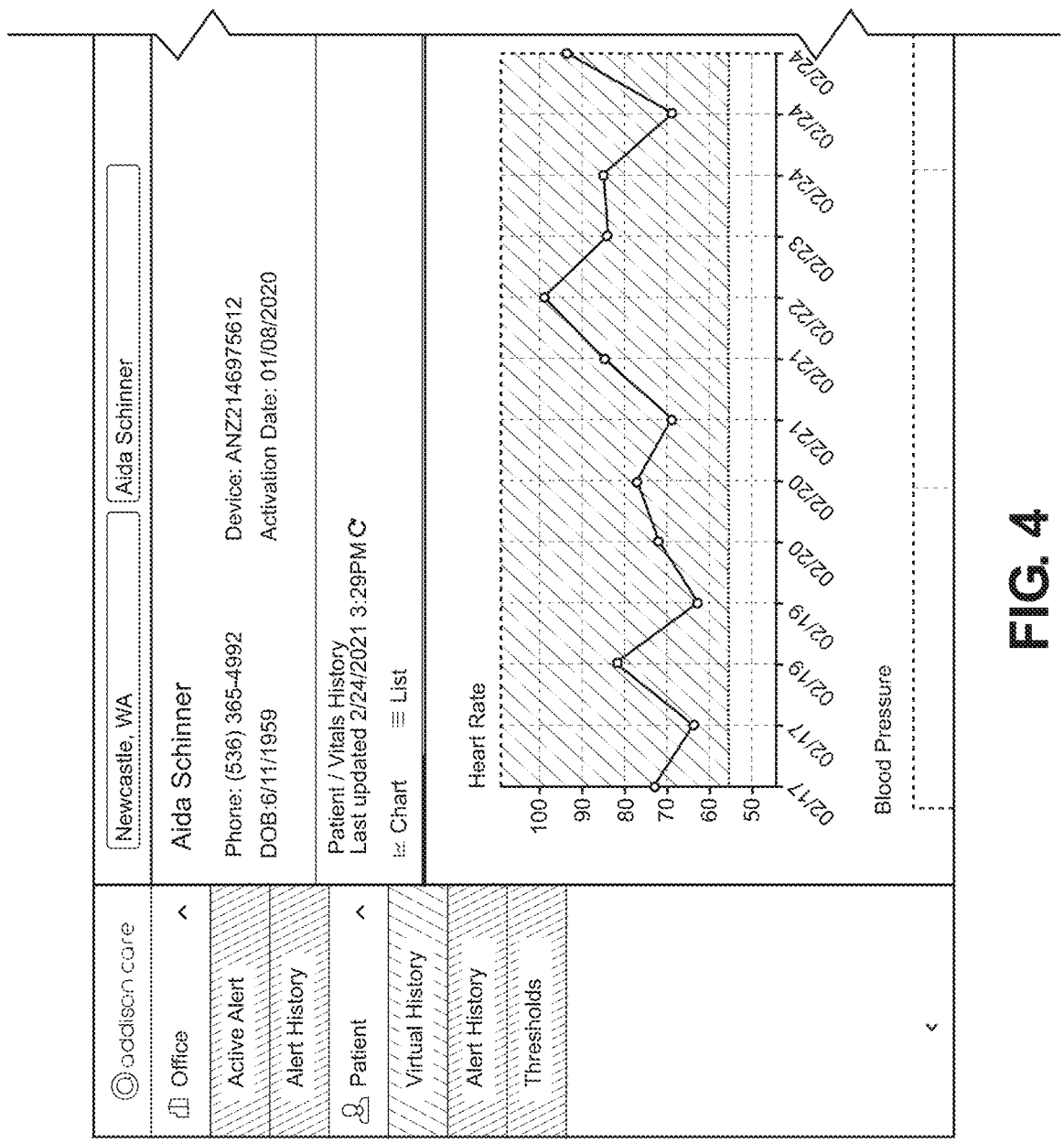
FIG. 4 is a depiction of a graphical user interface (GUI) after healthcare provider sign-in according to exemplary systems and methods of the present technology.
Figure 4:
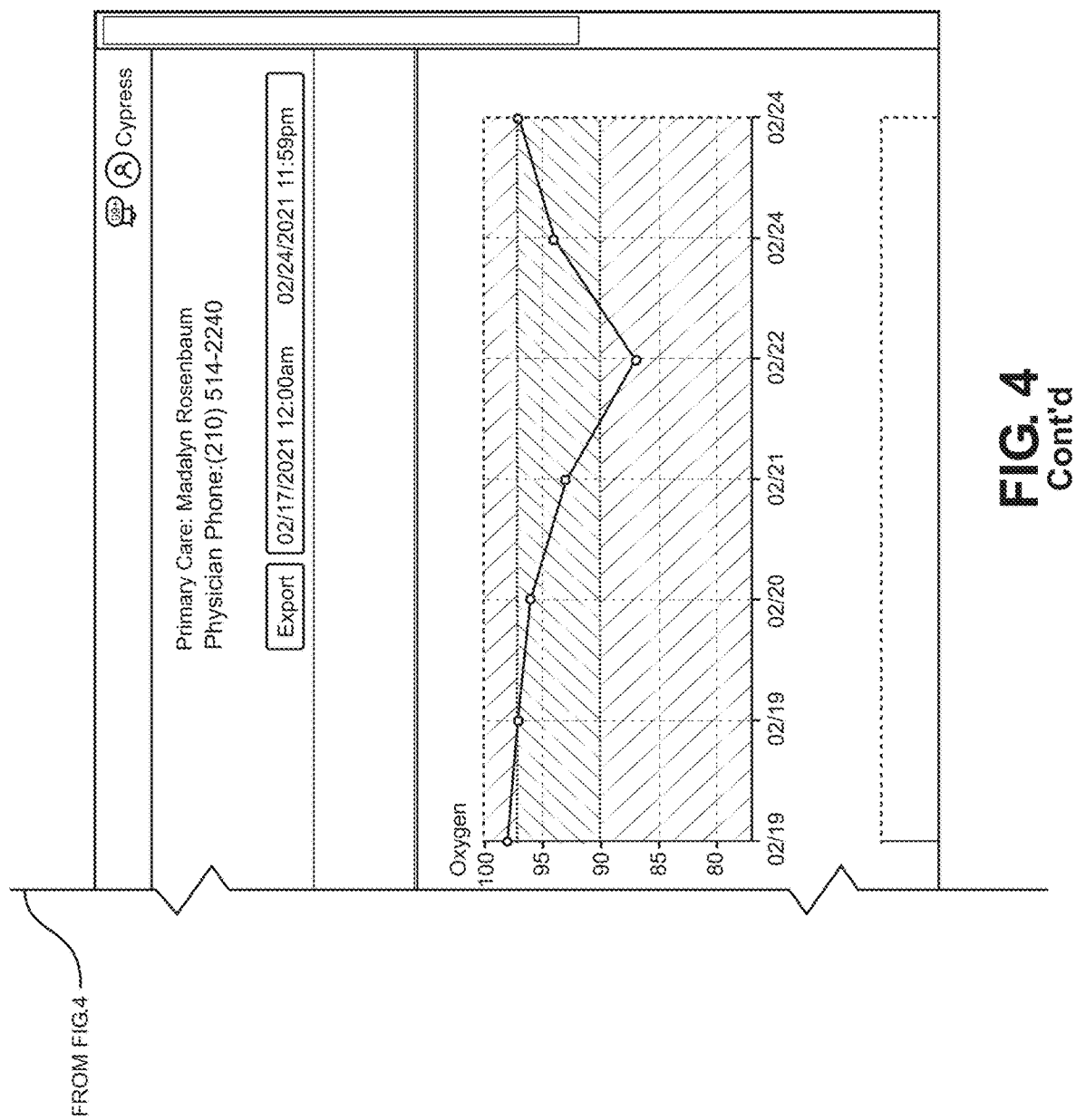

FIG. 4 is a depiction of a graphical user interface (GUI) after healthcare provider sign-in according to exemplary systems and methods of the technology.

The platform serves to deliver data to a provider accessible content delivery system with an integrated graphical user interface (GUI). This interface is depicted in FIG. 4. FIG. 4 shows the GUI landing page following the healthcare provider's sign-in. As shown, once signed-in, healthcare providers can choose between office and patient viewing modes. When in office mode, healthcare providers can view all current active alerts resulting from the detection of anomalous data for which they have yet to respond (active alerts as per FIG. 3), or they can view a history of alerts they have reviewed and addressed across all patients. When in patient mode and following the selection of a patient from the user library, healthcare providers may choose to review the vitals history for that specific patient as depicted in FIG. 4, review the alert history for that specific patient, and/or modify the current threshold for anomalies based on patient performance across their care plan. Once thresholds are modified, the system is immediately updated to include the newly defined acceptable range for that specific patient throughout the previously outlined anomaly detection process.

Real-Time Risk Stratification

As health data from the user are ingested into the platform, they are immediately integrated into existing data stores which contain additional information related to the user's current plan of care. These additional data include aspects of concurrent diagnoses, health resource utilization, lab results and medical test data, age, and more. As ingested data are integrated and analyzed in real-time, the additional features allow for classification algorithms to perform real-time risk stratification for the user's capacity for self-managed care. These risk strata include high risk, moderate risk, mild risk and low risk and are defined as the user's capacity for successful self-management of their current disease states. Following risk-stratification of the user, healthcare providers are informed of the resulting output via the previously described GUI and can coordinate with the user's care team to remotely provide the most appropriate recommendation for care delivery need, location, time and frequency.

Secure Electronic Medical Records Integration

While the platform supports care plan management and decision-making process in remote care settings, it is also necessary to integrate data from the remote setting back into the traditional brick-and-mortar setting via electronic medical records (EMRs). By integrating relational data storage and secure endpoints, all remotely collected data are also able to be pulled from and pushed to existing EMR systems in the healthcare providers' setting. These remotely collected data are routed back to existing EMR systems via compliant Fast Healthcare Interoperability Resources (FHIR) application programming interfaces (API), allowing remotely collected data to be integrated into the user's electronic health records and included for review in on-site assessments conducted by healthcare providers.

FIG. 5 is a depiction of an exemplary secure intelligent networked architecture 500 according to exemplary systems and methods of the present technology.

FIG. 5 shows a secure intelligent networked architecture 500 for real-time precision care plan remote support including a secure intelligent data receiving agent 505 having a specialized hardware processor and a memory, the secure intelligent data receiving agent 505 configured to automatically receive a digital data element over a network 520 from a Bluetooth® equipped peripheral device 525. The digital data element may represent an output (e.g., vital sign, exercise action, etc.) in response to a predetermined plan (e.g., doctor's orders, a prescription, exercise plan, etc.). The secure intelligent data receiving agent 505 caches the digital data element within a non-relational database (e.g., as shown in FIG. 1) for short term storage. The secure intelligent data receiving agent 505 is configured to process the digital data element using a serverless compute functionality (e.g., as shown in FIG. 1) and configured with logic for anomaly detection (e.g., as shown in FIG. 2).

The secure intelligent networked architecture 500 for real-time precision plan remote support further comprises a secure intelligent data storage agent 515 having a specialized hardware processor and a memory, the secure intelligent data storage agent 515 configured to automatically store the digital data element if it is associated with a non-anomalous and/or anomalous detection. The secure intelligent networked architecture 500 for real-time precision plan remote support includes the logic for anomaly detection (e.g., as shown in FIG. 2) configured to place the digital data element into a range if it is associated with a non-anomalous and/or anomalous detection. The logic for anomaly detection is also configured to adjust the range for a plurality of patients and configured to adjust the range for a single patient.

In further exemplary embodiments, the secure intelligent data receiving agent 505 is configured with electronic healthcare records for a plurality of patients and is configured to perform a risk stratification for a patient's capacity for self-managed care. In some exemplary embodiments, the risk stratification includes high risk, moderate risk, mild risk and low risk as the patient's capacity for successful self-management of the patient's current disease state.

Also provided is an interactive touchscreen graphical user interface-based content delivery system (e.g., as shown in FIG. 1) configured for interpretation of the digital data element if it is associated with an anomalous and/or non-anomalous determination. The logic for anomaly detection is also configured to simultaneously route the digital data element through the logic for anomaly detection a second time, through a cloud-based service 510 for long-term storage and analysis, and to automatically notify a content delivery network (e.g., as shown in FIG. 1) if it is associated with an anomalous determination. Exemplary embodiments include the integration of a remotely collected digital data element and an electronic healthcare record within the secure intelligent data receiving agent 505 by way of an encrypted application programming interface ("API") (e.g., as shown in FIG. 1).

In various exemplary embodiments, the output may include temperature, oxygen saturation, weight, blood glucose level, or blood pressure data. The Bluetooth® equipped peripheral device 525 may be a glucose monitor, thermometer, pulse oximeter, blood pressure monitor, spirometer or a scale, and may be equipped with a hardware processor. Furthermore, the predetermined plan may be stored on a networked computing device (e.g., mobile phone, tablet, exercise monitor, etc.) and the secure intelligent data receiving agent 505 may be configured to change the predetermined plan based on the output. The secure intelligent data receiving agent 505 may be configured to change the predetermined plan based on the anomaly or non-anomaly and the secure intelligent data receiving agent may be configured to change the predetermined plan based on the stratification. Additionally, the secure intelligent data receiving agent may be configured to change the predetermined plan based on a range.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed:

1. A secure intelligent networked architecture for real-time precision care plan remote support comprising:

a secure intelligent data receiving agent having a specialized hardware processor and a memory, the secure intelligent data receiving agent configured to automatically receive a digital data element over a network from a wireless transmission-equipped peripheral device, the digital data element representing an output in response to a predetermined plan;
the secure intelligent data receiving agent configured to perform a risk stratification for a patient's capacity for self-managed care; and
the secure intelligent data receiving agent configured to process the digital data element and configured with logic for anomaly detection, the logic for the anomaly detection being executed by a machine learning model comprising:
at least one support vector machine classifier comprising a plurality of support vectors, the at least one support vector machine classifier configured to detect anomalies by classifying outlier data;
a plurality of input training vectors determined from one or more outcomes from the anomaly detection;
a plurality of input measurements over a number of days;
support vector classification finding a hyperplane, the plurality of support vectors representing data points closest to the hyperplane and defining a decision boundary;
a kernel transforming the plurality of input measurements that support the finding of the hyperplane;
parameter c, a regularization parameter in the support vector classification that controls a trade-off between maximizing a distance between the hyperplane and a nearest data point of a class; and
the plurality of input measurements and corresponding predicted outcomes tested for a predictive performance of the logic for the anomaly detection.

2. The secure intelligent networked architecture for real-time precision care plan remote support of claim 1, further comprising a secure intelligent data storage agent having a specialized hardware processor and a memory, the secure intelligent data storage agent configured to automatically store the digital data element if it is associated with a non-anomalous determination.

3. The secure intelligent networked architecture for real-time precision care plan remote support of claim 2, further comprising the logic for the anomaly detection configured to place the digital data element into a range if it is associated with the non-anomalous determination.

4. The secure intelligent networked architecture for real-time precision care plan remote support of claim 1, further comprising the logic for the anomaly detection configured to place a plurality of digital data elements into a range if it is associated with a non-anomalous determination.

5. The secure intelligent networked architecture for real-time precision care plan remote support of claim 4, further comprising the logic for the anomaly detection configured to adjust the range for a plurality of patients.

6. The secure intelligent networked architecture for real-time precision care plan remote support of claim 4, further comprising the logic for the anomaly detection configured to adjust the range for a single patient.

7. The secure intelligent networked architecture for real-time precision care plan remote support of claim 1, further comprising the secure intelligent data receiving agent configured with electronic healthcare records for a plurality of patients.

8. The secure intelligent networked architecture for real-time precision care plan remote support of claim 1, the risk stratification including high risk, moderate risk, mild risk and low risk as the patient's capacity for successful self-management of the patient's current disease state.

9. The secure intelligent networked architecture for real-time precision care plan remote support of claim 1, further comprising an interactive touchscreen graphical user interface-based content delivery system configured for interpretation of the digital data element if it is associated with an anomalous determination.

10. The secure intelligent networked architecture for real-time precision care plan remote support of claim 1, further comprising an interactive touchscreen graphical user interface-based content delivery system configured for interpretation of the digital data element if it is associated with a non-anomalous determination.

11. The secure intelligent networked architecture for real-time precision care plan remote support of claim 1, further comprising the logic for the anomaly detection configured to simultaneously route the digital data element through the logic for the anomaly detection a second time, through a cloud-based service for long-term storage and analysis, and to automatically notify a content delivery network if it is associated with an anomalous determination.

12. The secure intelligent networked architecture for real-time precision care plan remote support of claim 1, further comprising integration of a remotely collected digital data element and an electronic healthcare record within the secure intelligent data receiving agent by way of an encrypted application programming interface ("API").

13. The secure intelligent networked architecture for real-time precision care plan remote support of claim 1, the output further comprising any of temperature, oxygen saturation, weight, blood glucose level, or blood pressure data.

14. The secure intelligent networked architecture for real-time precision care plan remote support of claim 1, further comprising the wireless transmission-equipped peripheral device being any of a glucose monitor, thermometer, pulse oximeter, blood pressure monitor, spirometer or a scale.

15. The secure intelligent networked architecture for real-time precision care plan remote support of claim 1, further comprising the wireless transmission-equipped peripheral device having a hardware processor.

16. The secure intelligent networked architecture for real-time precision care plan remote support of claim 1, further comprising a predetermined plan being stored on a networked computing device.

17. The secure intelligent networked architecture for real-time precision care plan remote support of claim 16, further comprising the secure intelligent data receiving agent configured to change the predetermined plan based on the output.

18. The secure intelligent networked architecture for real-time precision care plan remote support of claim 16, further comprising the secure intelligent data receiving agent configured to change the predetermined plan based on an anomaly or non-anomaly.

19. The secure intelligent networked architecture for real-time precision care plan remote support of claim 16, further comprising the secure intelligent data receiving agent configured to change the predetermined plan based on a stratification.

20. The secure intelligent networked architecture for real-time precision care plan remote support of claim 16, further comprising the secure intelligent data receiving agent configured to change the predetermined plan based on a range.

* * * * *